US00PP19782P2

(12) United States Plant Patent
Danziger

(10) Patent No.: US PP19,782 P2
(45) Date of Patent: Mar. 3, 2009

(54) ***SUTERA* PLANT NAMED 'DANCOP27'**

(50) Latin Name: *Sutera cordata*
Varietal Denomination: DANCOP27

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,421

(22) Filed: Jan. 11, 2008

(51) Int. Cl.
*A01H 5/00* (2006.01)

(52) U.S. Cl. ..... Plt./485

(58) Field of Classification Search ..... Plt./485, Plt./263
See application file for complete search history.

*Primary Examiner*—Annette H Para
*Assistant Examiner*—S. B. McCormick-Ewoldt

(57) ABSTRACT

A new and distinct *Sutera* cultivar named 'DANCOP27' is disclosed, characterized by having large, pink flowers, with a distinctive purple center halo, a compact, mounded and upright plant habit and continuous flowering. The new variety is a *Sutera*, normally produced as an outdoor garden or container plant.

2 Drawing Sheets

Latin name of the genus and species: *Sutera cordata.*
Variety denomination: 'DANCOP27'.

BACKGROUND OF THE INVENTION

The new *Sutera* cultivar is a product of a planned breeding program conducted by the inventor, Gabriel Danziger, in Moshav Mishmar Hashiva, Israel. The objective of the breeding program was to produce plants of *Sutera cordata* with compact habits and large pink flowers. The seed parent is the unpatented, proprietary seedling variety referred to as *Sutera cordata* cv.5-259. The pollen parent is unknown as 'DANCOP27' is a result of a plannned open pollination in which the pollen parent is impossible to distinguish.

The new variety was discovered in May 2006 by the inventor, in a group of seedlings resulting from that crossing, in Moshav Mishmar Hashiva, Israel.

Asexual reproduction of the new cultivar 'DANCOP27' by vegetative cuttings was first performed at a commercial greenhouse in Moshav Mishmar Hashiva, Israel in June 2006 and has shown that the unique features of this cultivar are stable and reproduced true to type in successive generations.

SUMMARY OF THE INVENTION

The cultivar 'DANCOP27' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP27' These characteristics in combination distinguish 'DANCOP27' as a new and distinct *Sutera* cultivar:

1. Compact plant habit.
2. Very large flowers.
3. Unique pink flower coloration, with a darker ring near the corolla tube.
4. Trailing plant habit.

Plants of the new cultivar 'DANCOP27' are similar to plants of the seed parent, *Sutera cordata* 'cv.5-259' in most horticultural characteristics, however, plants of the new cultivar 'DANCOP27' produce lighter pink flowers, with a distinct purple halo. Additionally, plants of the new variety are of a more mounded plant habit than the female parent.

COMMERCIAL COMPARISON

Plants of the new cultivar 'DANCOP27' are similar to plants of the commercial variety 'DANCOP19, ' U.S. Plant Pat. No. 18,116 in most horticultural characteristics, however, plants of the new cultivar 'DANCOP27' have larger flowers, of a lighter pink, with a darker halo in the center. The new variety also has a more trailing plant habit and larger leaves than 'DANCOP19.'

BRIEF DESCRIPTION OF THE PHOTOGRAPH

Figure 1:
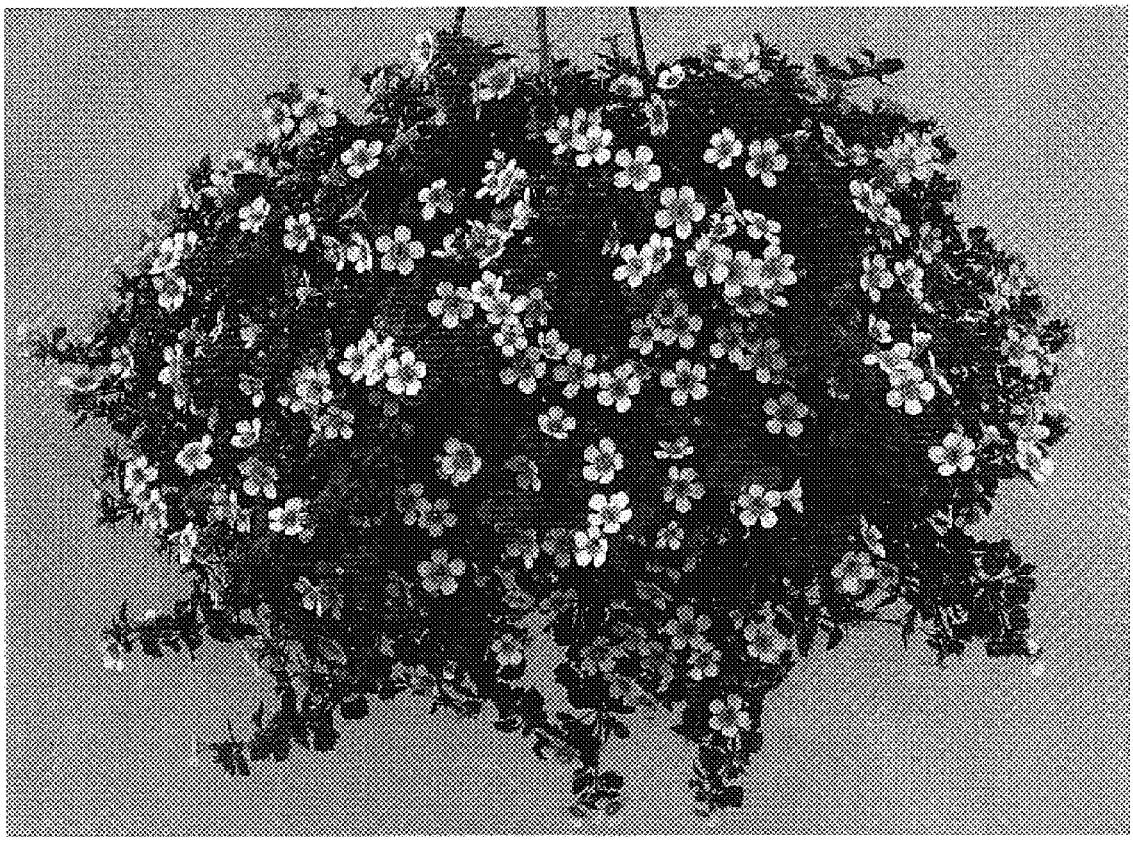

The accompanying photograph in FIG. 1 illustrates in full color a typical plant of 'DANCOP27' grown in a greenhouse, in a 13 cm basket. Age of the plant photographed is approximately 3 months from a rooted cutting.

Figure 2:
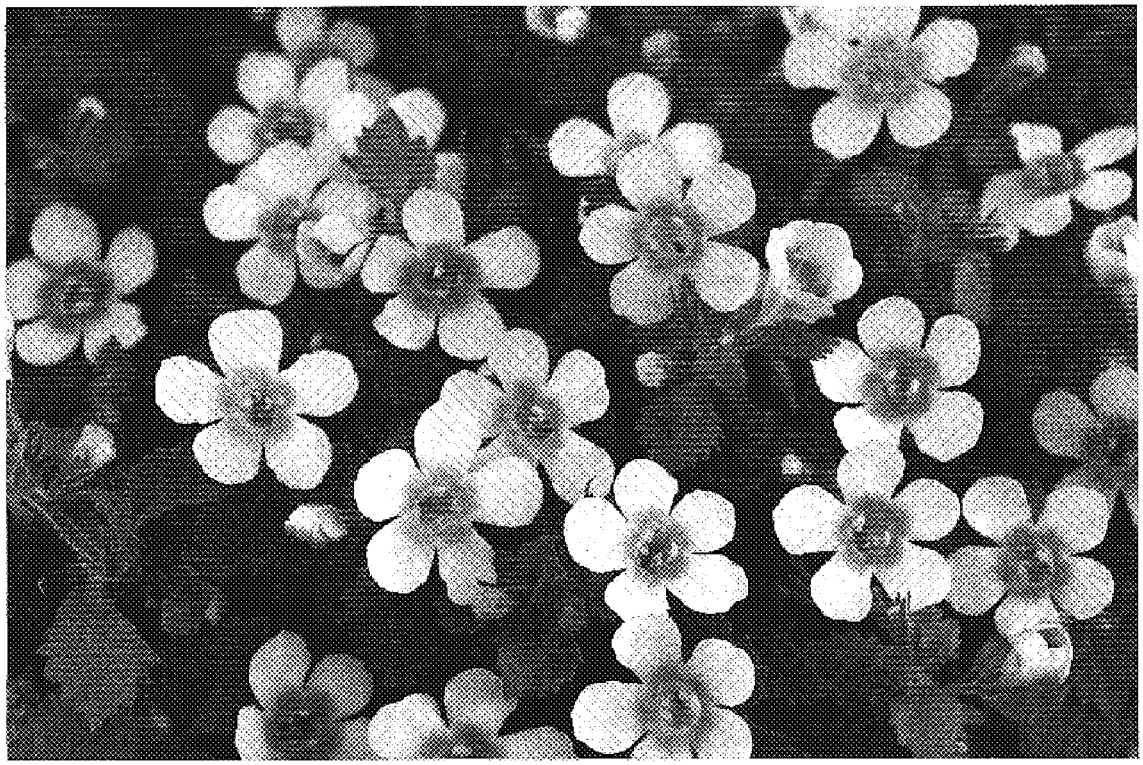

FIG. 2 illustrates in full color a close up of a typical bloom of 'DANCOP27.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary siginificance are used. The following observations and measurements describe 'DANCOP27' 3 month old plants grown in a greenhouse in Moshav Mishmar Hashiva, Israel. The growing temperature ranged from 18° C. to 24° C. The greenhouse is subject to partial shade. General light conditions are bright, normal sunlight, with some shade during the brightest part of the day. Measurements and numerical values represent averages of typical plant types.

Botanical classification: *Sutera cordata* cultivar 'DANCOP27.'

PROPAGATION

Time to initiate roots: About 7 to 10 days at approximately 18° C.
Root description: Fine, densely fibrous.

PLANT

Growth habit: Mounding annual.
Pot size of plant described: 13 cm.
Age of plant described: Approximately 90 days from a rooted cutting.
Height:
*To top of flowers.*—Approximately 12 cm.
Plant spread: Approximatrly 55 cm.
Growth rate: Rapid.
Branching characteristics: Very well-branched.
Length of primary lateral branches: Approximately 40 cm.
Diameter of lateral branches: Approximately 0.2 cm.
Quantity of primary lateral branches: About 8.
Characteristics of primary lateral branches:
*Form.*—Cylindrical.
*Diameter.*—Approximately 0.2 cm.
*Color.*—Near RHS Yellow-Green 146B.
*Texture.*—Velvety.
*Strength.*—Strong.
Internode length: Approximately 2 cm.

FOLIAGE

Leaf:
*Arrangement.*—Opposite.
*Quantity.*—Approximately 100 per branch.
*Average length.*—Approximately 2.5 cm.
*Average width.*—Approximately 1.6 cm.
*Shape of blade.*—Ovate.
*Apex.*—Obtuse.
*Base.*—Acute.
*Margin.*—Serrate.
*Texture of top surface.*—Velvety.
*Pubescence.*—Slightly pubescent.
*Aspect.*—Horizontal.
*Color.*—Young foliage upper side: Near RHS Green 137A. Young foliage under side: Near RHS Green 137C. Mature foliage upper side: Near RHS Yellow-Green 147A. Mature foliage under side: Near RHS Yellow-Green 147B.
*Venation.*—Type: Pinnate. Venation color upper side: Near RHS Yellow-Green 147A. Venation color under side: Near RHS Yellow-Green 147B.
*Petiole.*—Length: Approximately 0.6 cm. Diameter: Approximately 0.1 cm. Color: Near RHS Yellow-Green 147A. Texture: Velvety.

FLOWER

Natural flowering season: Freely flowering all year in Moshav Mishmar Hashiva Israel. Begins flowering approximately 4 weeks after planting a rooted cutting.
Inflorescence and flower type and habit: Salverform.
Rate of flower opening: About 3 days from bud to fully opened flower.
Flower longevity on plant: Individual flowers last 3 days on the plant.
Quantity of flowers: About 200 fully opened flowers per plant.
Flower form: Salverform.
Flower size:
*Diameter.*—Approximately 2 cm.
*Length.*—Approximately 1.5 cm.
*Corolla tube diameter.*—Approximately 0.3 cm.
Corolla/petals:
*Arrangement.*—5 rounded and gameopetalous petals.
*Lobe length.*—About 0.8 cm.
*Lobe width.*—About 0.6 cm.
*Quantity.*—5.
*Texture.*—Velvety.
*Lobe apex.*—Rounded.
*Lobe shape.*—Rounded.
*Margin.*—Entire.
*Aspect.*—Slanted upward.
Color:
*When opening.*—Upper surface: Near RHS Purple 75C, with a center halo of Purple 77B. Lower surface: Near RHS Purple 76B.
*Fully opened.*—Upper surface: Near RHS Purple 75D with a center halo of Purple 77B. Lower surface: Near RHS Purple 76B.
*Corolla tube color.*—Near RHS Red-Purple 65D.
Bud:
*Shape.*—Slightly flattened sphere.
*Length.*—Approximately 1 cm.
*Diameter.*—Approximately 0.5 cm.
*Color.*—Near RHS Purple 76A.
Calyx/sepals:
*Quantity per flower.*—5, fused at base.
*Shape.*—Linear.
*Length.*—Approximately 0.6 cm.
*Width.*—Approximately 0.1 cm.
*Apex.*—Acute.
*Base.*—Fused.
*Margin.*—Entire.
*Texture.*—Velvety.
*Color.*—Upper Surface: Near RHS Green 137C. Lower Surface: Near RHS Green 137C.
Peduncle: None.
Pedicel:
*Length.*—Approximately 0.5 cm.
*Diameter.*—Approximately 0.1 cm.
*Color.*—Near RHS Yellow-Green 146B.
*Orienation.*—Slanted upward at an angle of about 45°.
*Pubescence.*—Slight.
Fragrance: None.

REPRODUCTIVE ORGANS

Stamens:
*Number.*—4.
*Filament length.*—Approximately 1 cm.
Anthers:
*Shape.*—Cylindrical.
*Length.*—Approximately 0.1 cm.
*Color.*—Near RHS Yellow 6B.
*Pollen.*—Color: Near RHSYellow 6C. Quantity: Moderate.
Pistil:
*Number.*—1.
*Length.*—Approximately 1.2 cm.

*Style.*—Length: Approximately 1.3 cm. Color: Near RHS Yellow-Green 1B.

*Stigma.*—Shape: Round. Color: Near RHS Yellow-Green N144B. Ovary Color: Near R.H.S. Green 143B.

OTHER CHARACTERISTICS

Seeds and fruits: Not observed and not commercially important.

Disease/pest resistance: Neither resistance nor susceptibility to pathogens and pests common to *Sutera* have been observed.

Temperature tolerance: The new variety tolerates temperatures between 5 to 35° C.

What is claimed is:

1. A new and distinct cultivar of *Sutera* plant named 'DANCOP27' as herein illustrated and described.

* * * * *